United States Patent
Nehrke et al.

(10) Patent No.: US 10,222,437 B2
(45) Date of Patent: Mar. 5, 2019

(54) MR IMAGING WITH TEMPERATURE MAPPING

(71) Applicant: KONINKLIJKE PHILIPS N.V., Eindhoven (NL)

(72) Inventors: Kay Nehrke, Hamburg (DE); Peter Bornert, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 355 days.

(21) Appl. No.: 15/030,430

(22) PCT Filed: Oct. 14, 2014

(86) PCT No.: PCT/EP2014/071992
§ 371 (c)(1),
(2) Date: Apr. 19, 2016

(87) PCT Pub. No.: WO2015/059000
PCT Pub. Date: Apr. 30, 2015

(65) Prior Publication Data
US 2016/0252595 A1   Sep. 1, 2016

(30) Foreign Application Priority Data

Oct. 21, 2013  (EP) .................................... 13189453

(51) Int. Cl.
*G01R 33/48* (2006.01)
*A61B 5/055* (2006.01)
*G01R 33/561* (2006.01)

(52) U.S. Cl.
CPC .......... *G01R 33/4804* (2013.01); *A61B 5/055* (2013.01); *G01R 33/4814* (2013.01); *G01R 33/4828* (2013.01); *G01R 33/5611* (2013.01)

(58) Field of Classification Search
CPC ............................ G01R 33/4804; A61B 5/055
(Continued)

(56) References Cited

U.S. PATENT DOCUMENTS

| 4,833,407 A | 5/1989 | Holland |
| 5,378,985 A * | 1/1995 | Hinks ............. G01R 33/56554 324/307 |

(Continued)

FOREIGN PATENT DOCUMENTS

| EP | 2615470 A1 | 7/2013 |
| WO | 2012117303 A1 | 9/2012 |

OTHER PUBLICATIONS

Rieke et al "Referenceless PRF Shift Thermometry" Magnetic Resonance in Medicine, vol. 51, p. 1223-1231.
(Continued)

*Primary Examiner* — Reena Aurora (57) ABSTRACT

The invention relates to a method of MR imaging of an object (10) placed in the examination volume of a MR device (1). It is the object of the invention to provide an improved MR-based temperature mapping method. The method of the invention comprises the steps of: subjecting the object (10) to an imaging sequence of RF pulses and switched magnetic field gradients, which imaging sequence is a stimulated echo sequence including: a) at least two preparation RF pulses ($\alpha$) radiated toward the object (10) during a preparation period (21), and b) one or more reading RF pulses ($\beta$) radiated toward the object (10) during an acquisition period (22) temporally subsequent to the preparation period (21); acquiring at least two MR signals during the acquisition period (22), wherein the two MR signals are either (i) a FID signal ($I_1$, FID) and a stimulated echo signal ($I_2$) or (ii) two stimulated echo signals (STE, STE*); and deriving a temperature map indicating the spatial distribution of the temperature within the object (10) from the at least two acquired MR signals. Moreover, the invention relates to a MR device (1) and to a computer program for a MR device (1).

20 Claims, 3 Drawing Sheets (58) Field of Classification Search
USPC .......................................................... 324/309
See application file for complete search history.

(56) References Cited

U.S. PATENT DOCUMENTS

| | | |
|---|---|---|
| 5,711,300 A | 1/1998 | Schneider et al. |
| 9,977,106 B2 | 5/2018 | Nehrke et al. |
| 9,977,108 B2 | 5/2018 | Nehrke et al. |
| 2013/0154642 A1* | 6/2013 | Sueoka ............ G01R 33/34015 324/309 |

OTHER PUBLICATIONS

Eggers et al "Dual-Echo Dixon Imaging With Flexible Choice of Echo Times" MRM 2011 65 p. 96-107.

Berglund et al "Two Point Dixon Method With Flexible Echo Times" MRM 2011 vol. 65, p. 994-1004.

Kay Nehrke et al "Dream a Novel Approach for Robust Ultrafast Multislice B1 Mapping" MRM Jan. 17, 2012.

Hsu et al "Encoding to the Longitudinal Magnetization for MR Imaging and Flow Velocity Mapping" Journal of Magnetic Resonance vol. 183, No. 1 Nov. 1, 2006 p. 41-49.

* cited by examiner

MR IMAGING WITH TEMPERATURE MAPPING

CROSS REFERENCE TO RELATED APPLICATIONS

This application is a U.S. national phase application of International Application No. PCT/EP2014/071992, filed on Oct. 14, 2014, which claims the benefit of EP Application Serial No. 13189453.7 filed on Oct. 21, 2013 and is incorporated herein by reference.

FIELD OF THE INVENTION

The invention relates to the field of magnetic resonance (MR) imaging. It concerns a method of MR imaging of an object. The invention also relates to a MR device and to a computer program to be run on a MR device.

BACKGROUND OF THE INVENTION

Image-forming MR methods which utilize the interaction between magnetic fields and nuclear spins in order to form two-dimensional or three-dimensional images are widely used nowadays, notably in the field of medical diagnostics, because for the imaging of soft tissue they are superior to other imaging methods in many respects, do not require ionizing radiation and are usually not invasive.

According to the MR method in general, the body of the patient to be examined is arranged in a strong, uniform magnetic field ($B_0$ field) whose direction at the same time defines an axis (normally the z-axis) of the co-ordinate system on which the measurement is based. The magnetic field produces different energy levels for the individual nuclear spins in dependence on the magnetic field strength which can be excited (spin resonance) by application of an electromagnetic alternating field (RF field, also referred to as $B_1$ field) of defined frequency (so-called Larmor frequency, or MR frequency). From a macroscopic point of view the distribution of the individual nuclear spins produces an overall magnetization which can be deflected out of the state of equilibrium by application of an electromagnetic pulse of appropriate frequency (RF pulse) while the magnetic field extends perpendicular to the z-axis, so that the magnetization performs a precessional motion about the z-axis. The precessional motion describes a surface of a cone whose angle of aperture is referred to as flip angle. The magnitude of the flip angle is dependent on the strength and the duration of the applied electromagnetic pulse. In the case of a so-called 90° pulse, the spins are deflected from the z axis to the transverse plane (flip angle 90°).

After termination of the RF pulse, the magnetization relaxes back to the original state of equilibrium, in which the magnetization in the z direction is built up again with a first time constant $T_1$ (spin lattice or longitudinal relaxation time), and the magnetization in the direction perpendicular to the z direction relaxes with a second time constant $T_2$ (spin-spin or transverse relaxation time). The variation of the magnetization can be detected by means of one or more receiving RF coils which are arranged and oriented within an examination volume of the MR device in such a manner that the variation of the magnetization is measured in the direction perpendicular to the z-axis. The decay of the transverse magnetization is accompanied, after application of, for example, a 90° pulse, by a transition of the nuclear spins (induced by local magnetic field inhomogeneities) from an ordered state with the same phase to a state in which all phase angles are uniformly distributed (dephasing). The dephasing can be compensated by means of a refocusing pulse (for example a 180° pulse). This produces an echo signal (spin echo) in the receiving coils.

In order to realize spatial resolution in the body, linear magnetic field gradients extending along the three main axes are superposed on the uniform magnetic field, leading to a linear spatial dependency of the spin resonance frequency. The signal picked up in the receiving coils then contains components of different frequencies which can be associated with different locations in the body. The MR signal data obtained via the RF coils corresponds to the spatial frequency domain and is called k-space data. The k-space data usually includes multiple lines acquired with different phase encoding. Each line is digitized by collecting a number of samples. A set of k-space data is converted to a MR image by means of Fourier transformation.

In a number of MR-guided diagnostic and therapeutic procedures, the measurement of tissue temperature is of particular importance. Thus, for example, in MR-HIFU ('magnetic resonance-guided high intensity focused ultrasound') applications, in which tissue is locally heated and destroyed by the focused irradiation of ultrasound energy, the local change of the temperature distribution needs to monitored during the procedure in order to be able to control the irradiation of ultrasound in a targeted manner. The heating regime must be adapted to keep the local temperature increase for the healthy tissue within allowable margins, while the target to be destroyed (for example a malignant tumor) is sufficiently heated. Besides MR-HIFU there are a number of other therapeutic procedures as well as diagnostic and functional MR studies, in which the spatial distribution of a change in temperature may be of interest and needs to be monitored.

One of the most sensitive MR-based temperature mapping approaches is the known proton resonance frequency shift (PRF) method (Rieke et al, Magnetic Resonance in Medicine, volume 51, pages 1223-1231). The magnetic resonance frequency of water protons changes as a function of temperature. Temperature changes induce slight variations of the bonding angles between the protons in the water molecules resulting in variations of the electronic shielding, resulting in a small change of the chemical shift. For a gradient echo acquisition performed at a given echo-time at two different temperatures a local change in the signal phase can be observed. A drawback is that the PRF method requires rather long echo times (in the order of $T_2^*$) for optimal sensitivity. Therefore, to allow real-time temperature mapping, typically spiral- or EPI-based fast MR signal readouts are used, which are prone to different kinds image artifacts (ghosting, blurring, image distortions, chemical shift-related artifacts etc.). Moreover, temperature maps acquired by the conventional PRF method, are prone to errors induced by different kinds of effects influencing the MR signal phase, such as patient/organ motion, overall system drift (RF, main field magnetic field, heating of the gradient coils etc.), eddy currents and so forth. Furthermore, the PRF method can be compromised by the signal composition within each individual voxel of the acquired MR image. Fat does not show the PRF effect. This can result in erroneous temperature change estimates in case both fat protons and water protons contribute to the MR signal within a single voxel. This is a particular problem in the context of MR-HIFU because MR-HIFU is typically applied in the abdominal chamber, where significant amounts of visceral fat may be present. Finally, flow represents a problem in PRF methods because flow-related phase artifacts may degrade the accuracy of the PRF shift measurements.

The European patent application EP 2 615 470 discloses that a stimulated echo acquisition preparation sequence is employed to encode phase-information. This approach is employed to encode the local flip angle from which the $B_1$-field distribution is derived.

SUMMARY OF THE INVENTION

From the foregoing it is readily appreciated that there is a need for an improved MR-based temperature mapping method.

In accordance with the invention, a method of MR imaging of an object placed in the examination volume of a MR device is disclosed. The method comprises the steps of:
- subjecting the object to an imaging sequence of RF pulses and switched magnetic field gradients, which imaging sequence is a stimulated echo sequence including:
  a) at least two preparation RF pulses radiated toward the object during a preparation period, and
  b) one or more reading RF pulses radiated toward the object during an acquisition period temporally subsequent to the preparation period;
- acquiring at least two MR signals during the acquisition period, wherein the two MR signals are either (i) a FID signal and a stimulated echo signal or (ii) two stimulated echo signals; and
- deriving a temperature map indicating the spatial distribution of the temperature within the object from the at least two acquired MR signals.

It is the gist of the invention to use a stimulated echo sequence as imaging sequence to measure the PRF shift. The imaging sequence may be simply tailored for PRF shift measurements. The PRF shift can be almost fully encoded during the preparation period, i.e. during stimulated echo preparation, and the MR signals can then be acquired in a very fast and robust gradient echo pulse train with a short repetition time of a few milliseconds during the acquisition period. Furthermore, the encoding of the PRF shift in the stimulated echo preparation makes the sequence of the invention very flexible with respect to different main magnetic field strength, because only the time interval between the two preparation RF pulses needs to be adapted to obtain the optimal temperature sensitivity.

The stimulated echo-based temperature mapping technique of the invention allows a temperature map to be acquired in a single shot of the stimulated echo sequence in about 100 ms duration, making this approach in principle real-time capable.

Since the temperature map can be acquired by means of a single repetition of the imaging sequence according to the invention, it is more robust against motion as compared to other known implementations of the PRF method.

Flow-induced phase errors are automatically reduced by the approach of the invention due to the low flow-sensitivity of the stimulated echo. However, in case of very strong flow, precautions can be taken to prepare the longitudinal magnetization before the application of the proposed sequence in such a way that flowing spins are appropriately suppressed. This can easily achieved by all kinds of known flow sensitive or so-called 'black-blood' magnetization preparation sequences.

It has to be noted that, due to the principles of the PRF shift method, the term 'temperature map' within the meaning of the invention does not necessarily refer to a map of absolute temperature as a function of spatial coordinates. It may as well refer to a map of relative temperature values indicating a temperature shift occurring, for example, between two successive measurements.

In general, a stimulated echo sequence comprises three (for example 60° or) 90° RF pulses, wherein the first two RF pulses are preparation pulses. The first preparation RF pulse transforms longitudinal nuclear magnetization into transverse nuclear magnetization. The second preparation RF pulse "stores" a fraction of the dephased transverse nuclear magnetization along the longitudinal axis. In case of 90° RF pulses this fraction is almost half of the dephased transverse magnetization. The third RF pulse is applied during the acquisition period which is temporally subsequent to the preparation period. The third RF pulse ("reading RF pulse") transforms the stored longitudinal nuclear magnetization into transverse nuclear magnetization again, thereby generating a so-called stimulated echo. Other RF refocused echoes are generated by this three RF pulse sequence, but those are not of interest here and may be suppressed by appropriate gradient switching. The stimulated echo MR signal together with the FID signal, which is also generated by the third RF pulse, can be acquired according to the invention and used for temperature mapping. MR imaging on the basis of stimulated echoes can be accelerated by replacing the third RF pulse by a train of low-flip angle reading RF pulses, wherein each reading RF pulse refocuses only a small portion of the longitudinal nuclear magnetization stored after the preparation period.

It has to be mentioned that the at least two preparation RF pulses used to store magnetization along the z-axis do not have to be of the same kind or flip angle. However, with respect to the mathematical treatment necessary to evaluate the measuring data, the choice of identical RF pulses and flip angles makes the formalism rather simple.

A plurality of FID signals and/or stimulated echo signals with appropriate phase encoding need to be acquired for generating a complete temperature map. Efficient sampling schemes like EPI, parallel imaging or compressed sensing can be advantageously applied for this purpose in combination with the invention.

In accordance with a preferred embodiment of the invention, the FID and/or the stimulated echo signals are acquired as gradient-recalled echo signals.

In a preferred embodiment of the invention, the temperature map is derived from the voxel-wise phase difference of the two acquired MR signals. For example, a MR image reconstructed from the acquired FID signals may serve as a reference to eliminate all phase shifts originating from the transmit/receive chain of the used MR apparatus. The voxel-wise temperature-induced phase shift can be determined from the product of one of the acquired MR signals and the complex conjugated other MR signal.

According to another preferred embodiment of the invention, the parameters of the imaging sequence (e.g. echo times, gradient strength) are selected such that signal contributions from water spins and signal contributions from fat spins superimpose in the acquired MR signals in such a way as to allow reconstruction of separate water and fat images. This enables to remove the signal contributions from fat spins and renders the technique robust against chemical shift-induced errors in the derived temperature map. The signal contributions from water spins and fat spins may be separated using a two- or multi-point Dixon technique. The relative contributions of different chemical species, such as water and fat, to the overall acquired MR signals can be calculated since information from two or more echo signals acquired at different echo times are available with the approach of the invention. This type of chemical shift encoding, when applied to the separation of the contributions of water and fat to the overall MR signal, is often referred to as Dixon-type of measurement. In its simplest form, the echo times are selected such that water and fat images are generated by either addition or subtraction of 'in phase' and 'out of phase' datasets. After separation of water and fat contributions, the temperature map can be derived according to the invention only from the signal contributions from water spins in the acquired MR signals. In this way, the 'fat contamination' of the PRF shift can be avoided. Moreover, the fat signal may be used as a reference to distinguish the temperature-induced PRF shift from, for example, a drift of the main magnetic field strength.

In another embodiment, the problem of fat contamination of the PRF shift may be addressed according to the invention by applying one or more fat saturation preparation RF pulses prior to the preparation RF pulses of the stimulated echo sequence. Alternatively, the stimulated echo sequence itself may be made spectrally selective to encode the water signal only. This can be achieved, for example, by replacing at least one of the preparation RF pulses (preferably the second one) by a spectrally selective RF pulse, to apply RF energy only to the water species. In principle, both stimulated echo preparation RF pulses and (not as efficiently) the RF pulses radiated during the acquisition period may be made chemical shift-selective to suppress the fat signal contribution.

According to a further preferred embodiment of the invention, the at least two preparation RF pulses each have a flip angle of 45°-90°. In this way, the amplitudes of the acquired stimulated echo signals are maximized which is advantageous in terms of signal-to-noise.

According to another preferred embodiment of the invention, a plurality of FID and/or stimulated echo MR signals are generated by means of a plurality of consecutive reading RF pulses, each having a flip angle of less than 90°, preferably less than 45°, most preferably less than 30°. As already mentioned above, a train of reading RF pulses having small flip angles can be used to achieve a fast readout of multiple FID and/or stimulated echo signals.

According to yet a further preferred embodiment of the invention, two stimulated echo signals, preferably a direct stimulated echo signal and a conjugate stimulated echo signal are acquired during the acquisition period. In this way, the sensitivity of the stimulated echo-based PRF measurement can be further increased. The two stimulated echo signals can be acquired at different echo times, wherein the stimulated echo and the conjugate stimulated echo are refocused from different coherences of the nuclear magnetization generated by the two preparation RF pulses. Preferably, the direct stimulated echo signal and the conjugate stimulated echo signal are acquired as gradient-recalled echo signals. This embodiment of the invention enables to derive the temperature map at a particularly long effective PRF encoding time.

The method of the invention described thus far can be carried out by means of a MR device including at least one main magnet coil for generating a uniform steady magnetic field within an examination volume, a number of gradient coils for generating switched magnetic field gradients in different spatial directions within the examination volume, at least one RF coil for generating RF pulses within the examination volume and/or for receiving MR signals from a body of a patient positioned in the examination volume, a control unit for controlling the temporal succession of RF pulses and switched magnetic field gradients, and a reconstruction unit for reconstructing MR images from the received MR signals. The method of the invention is preferably implemented by a corresponding programming of the reconstruction unit and/or the control unit of the MR device.

The method of the invention can be advantageously carried out in most MR devices in clinical use at present. To this end it is merely necessary to utilize a computer program by which the MR device is controlled such that it performs the above-explained method steps of the invention. The computer program may be present either on a data carrier or be present in a data network so as to be downloaded for installation in the control unit of the MR device.

BRIEF DESCRIPTION OF THE DRAWINGS

The enclosed drawings disclose preferred embodiments of the present invention. It should be understood, however, that the drawings are designed for the purpose of illustration only and not as a definition of the limits of the invention. In the drawings.

DETAILED DESCRIPTION OF THE EMBODIMENTS

Figure 1:
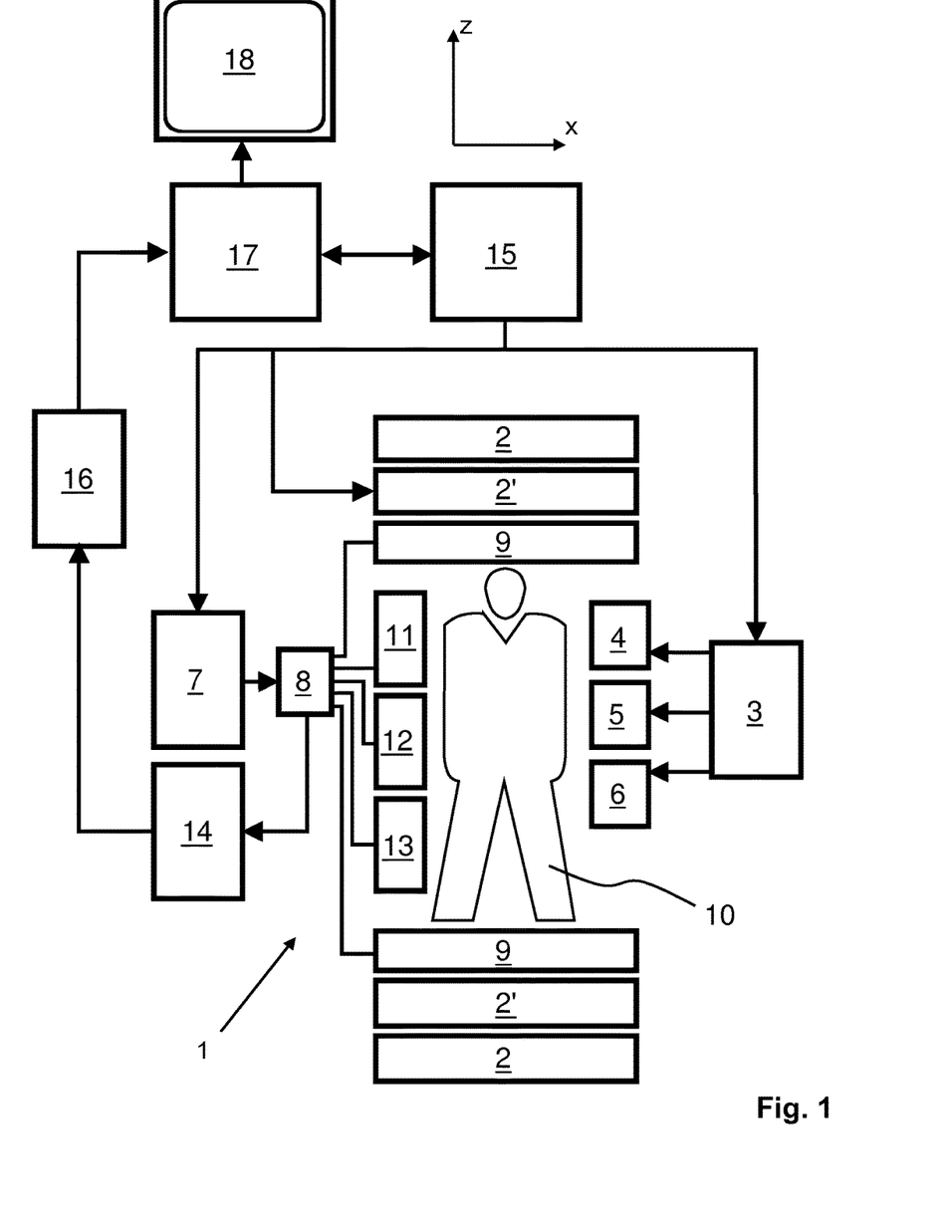
FIG. 1 schematically shows a MR device for carrying out the method of the invention.

With reference to FIG. 1, a MR device 1 is shown. The device comprises superconducting or resistive main magnet coils 2 such that a substantially uniform, temporally constant main magnetic field $B_0$ is created along a z-axis through an examination volume. The device further comprises a set of ($1^{st}$, $2^{nd}$, and—where applicable—$3^{rd}$ order) shimming coils 2', wherein the current flow through the individual shimming coils of the set 2' is controllable for the purpose of minimizing $B_0$ deviations within the examination volume.

A magnetic resonance generation and manipulation system applies a series of RF pulses and switched magnetic field gradients to invert or excite nuclear magnetic spins, induce magnetic resonance, refocus magnetic resonance, manipulate magnetic resonance, spatially and otherwise encode the magnetic resonance, saturate spins, and the like to perform MR imaging.

Most specifically, a gradient pulse amplifier 3 applies current pulses to selected ones of whole-body gradient coils 4, 5 and 6 along x, y and z-axes of the examination volume. A digital RF frequency transmitter 7 transmits RF pulses or pulse packets, via a send-/receive switch 8, to a body RF coil 9 to transmit RF pulses into the examination volume. A typical MR imaging sequence is composed of a packet of RF pulse segments of short duration which taken together with each other and any applied magnetic field gradients achieve a selected manipulation of nuclear magnetic resonance. The RF pulses are used to saturate, excite resonance, invert magnetization, refocus resonance, or manipulate resonance and select a portion of a body 10 positioned in the examination volume. The MR signals are also picked up by the body RF coil 9.

For generation of MR images of limited regions of the body 10 by means of parallel imaging, a set of local array RF coils 11, 12, 13 are placed contiguous to the region selected for imaging. The array coils 11, 12, 13 can be used to receive MR signals induced by body-coil RF transmissions. In parallel transmit applications, the array RF coils 11, 12, 13 may also be used for RF transmission, for example for the purpose of RF shimming.

The resultant MR signals are picked up by the body RF coil 9 and/or by the array RF coils 11, 12, 13 and demodulated by a receiver 14 preferably including a preamplifier (not shown). The receiver 14 is connected to the RF coils 9, 11, 12 and 13 via send-/receive switch 8.

A host computer 15 controls the current flow through the shimming coils 2' as well as the gradient pulse amplifier 3 and the transmitter 7 to generate any of a plurality of MR imaging sequences, such as echo planar imaging (EPI), echo volume imaging, gradient and spin echo imaging, fast spin echo imaging, and the like. For the selected sequence, the receiver 14 receives a single or a plurality of MR data lines in rapid succession following each RF excitation pulse. A data acquisition system 16 performs analog-to-digital conversion of the received signals and converts each MR data line to a digital format suitable for further processing. In modern MR devices the data acquisition system 16 is a separate computer which is specialized in acquisition of raw image data.

Ultimately, the digital raw image data is reconstructed into an image representation by a reconstruction processor 17 which applies a Fourier transform or other appropriate reconstruction algorithms, such like SENSE or SMASH. The MR image may represent a planar slice through the patient, an array of parallel planar slices, a three-dimensional volume, or the like. The image is then stored in an image memory where it may be accessed for converting slices, projections, or other portions of the image representation into appropriate format for visualization, for example via a video monitor 18 which provides a man-readable display of the resultant MR image.

Figure 2:
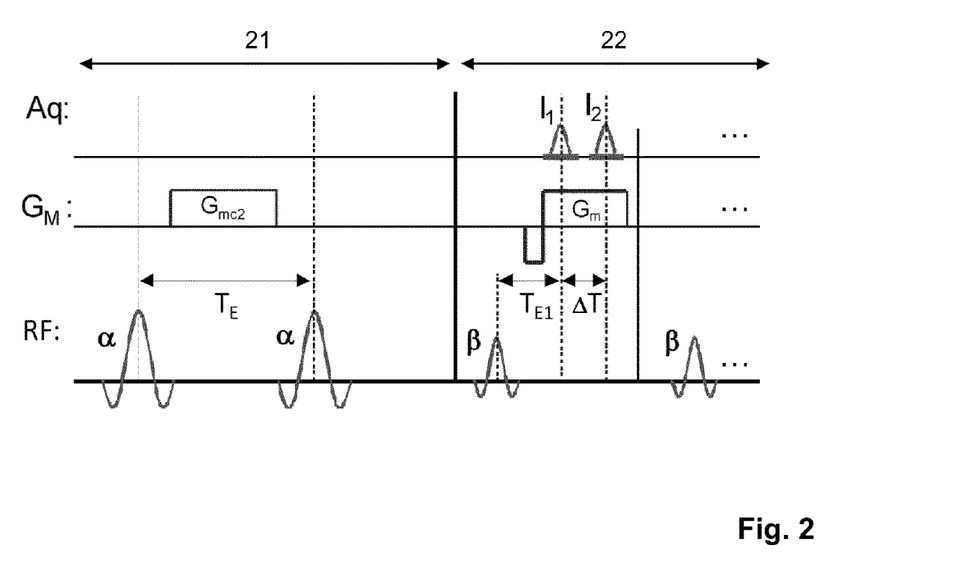
FIG. 2 shows a schematic diagram illustrating an imaging sequence according to the invention.

FIG. 2 shows a diagram illustrating an imaging sequence according to the invention. The depicted imaging sequence is a stimulated echo sequence which is subdivided into a preparation period 21 and an acquisition period 22. Two preparation RF pulses having a flip angle of α are applied during the preparation period 21. The two preparation RF pulses are separated by a time interval $T_E$. A de-phaser magnetic field gradient $G_{mc2}$ is applied between the two preparation RF pulses. A sequence of reading RF pulses having flip-angle β are generated during the acquisition period 22, which is temporally subsequent to the preparation period 21. An FID signal $I_1$ and a stimulated echo signal $I_2$ are acquired after each reading pulse as gradient-recalled echoes.

Directly after the preparation sequence 21, the longitudinal magnetization is given by:

$$M_{z1} = \cos^2(\alpha) \cdot M_0$$

$$M_{z2} = \frac{1}{2} \sin^2(\alpha) \cdot M_0,$$

wherein $M_{z1}$ and $M_{z2}$ denote the un-prepared (i.e. in-phase) and the stimulated echo-prepared (i.e. de-phased) longitudinal magnetization, respectively. In accordance with the invention, both the FID signal $I_1$ generated from $M_{z1}$ and the stimulated echo signal $I_2$ generated from $M_{z2}$ are acquired at different points in time $T_{E1}$ and $T_{E1}+\Delta T$, respectively. The delay $\Delta T$ between the two echoes $I_1$, $I_2$ is determined by the relation:

$$\Delta T = A_{mc2}/G_m,$$

wherein $A_{mc2}$ denotes the gradient-time area of the de-phaser gradient $G_{mc2}$ and $G_m$ denotes the strength of the readout magnetic field gradient. Neglecting $T_1$- and $T_2$-effects, the two acquired echo signals $I_1$ and $I_2$ are given by:

$$I_1 = S \cdot C(T_{E1}) \sin(\beta) M_{z1}$$

$$I_2 = S \cdot C(T_{E1}+\Delta T-T_E) \sin(\beta) M_{z2},$$

wherein S represents a complex system constant, which is equal for both echo signals $I_1$ and $I_2$ and which is determined e.g. by transmit and receive coil sensitivities for a given voxel. β is the nominal flip angle of the reading RF pulses. C describes the signal de-phasing for a given voxel due to the PRF shift:

$$C(t) = \int_V \rho(r) e^{-i\omega(r)t} dr,$$

wherein ρ and ρω denote the proton density and a temperature-induced frequency offset (PRF shift), respectively. The integral describes the summation over the given voxel. For the purpose of temperature mapping according to the invention, the temperature-induced phase shift may be determined from the product of the FID signal $I_1$ and the complex conjugated stimulated echo signal $I_2^*$:

$$\Phi = \arg(I_1 \cdot I_2^*)$$

Therein, the effective PRF shift encoding time $t_{PRF,eff}$ is:

$$t_{PRF,eff} = T_E - \Delta T$$

A temperature map can then be derived according to the PRF method for each voxel as the local temperature shift is proportional to the PRF phase shift:

$$\Delta T = \frac{\Phi}{\gamma \alpha B_0 t_{PRF,eff}}, \alpha \approx -0.01 \text{ ppm}/K,$$

wherein γ is the gyromagnetic ratio and $B_0$ is the strength of the main magnetic field.

Figure 3:
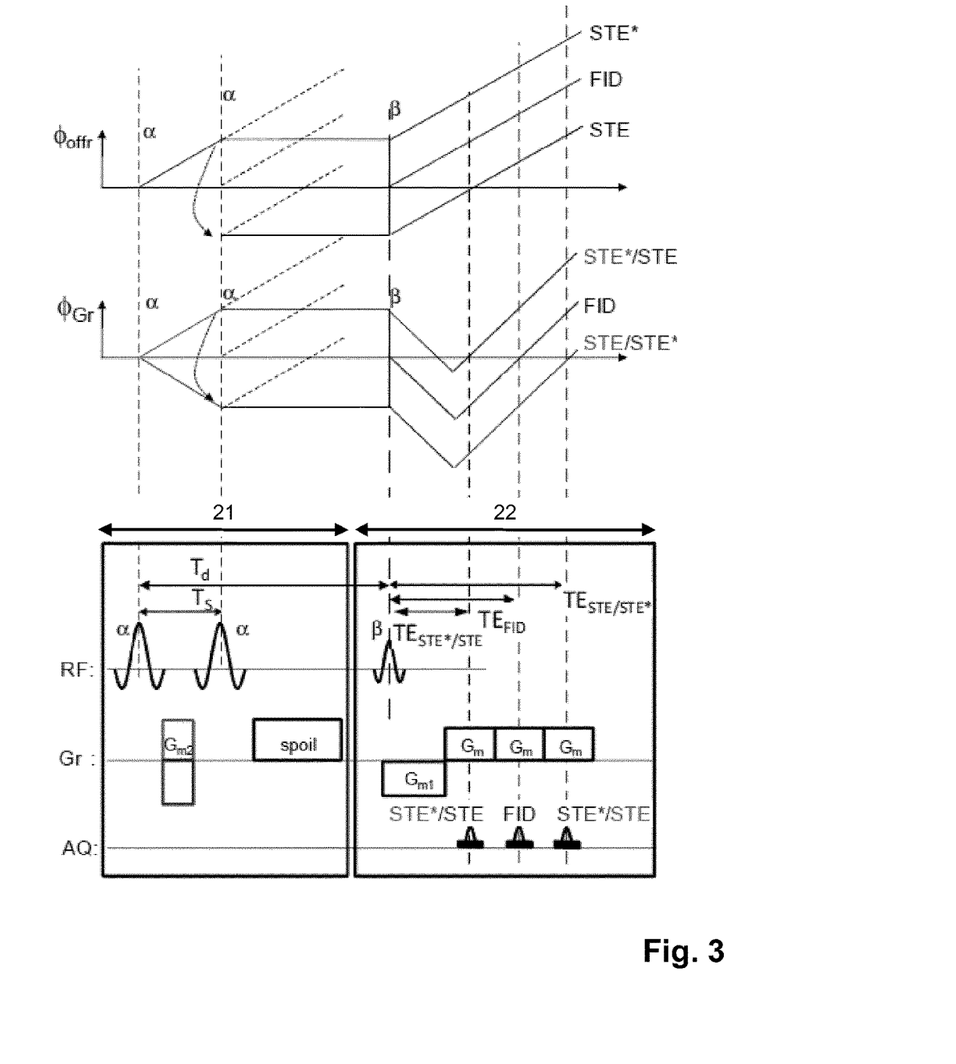
FIG. 3 shows a schematic diagram illustrating an imaging sequence according to another embodiment of the invention, in which direct and conjugate stimulated echo signals are acquired.

The sensitivity of the stimulated echo based PRF shift measurement can be increased by using a triple-echo acquisition as shown in FIG. 3.

FIG. 3 shows a diagram illustrating an imaging sequence according to another embodiment of the invention. The diagram shows the imaging sequence (bottom) along with phase graphs showing the coherence pathways for static, susceptibility-related gradients (top) and switched gradients (centre). The reading RF pulse sequence consists of a preparation period 21 and an acquisition period 22. The reading RF pulse β creates an FID signal, a stimulated echo STE* and a conjugate stimulated echo STE*, which are acquired as separate gradient-recalled echoes $I_{FID}$, $I_{STE}$ and $I_{STE^*}$. The acquisition order is determined by de-phaser gradient $G_{m2}$. The timing of the three gradient echoes is controlled by the switched gradients $G_{m1}$, $G_m$ (illustrated by the lower phase graph $\Phi_{Gr}$). The upper phase graph $\Phi_{off}$ illustrates the impact of static inhomogeneities, and, hence, the spectral encoding of the signals.

Directly after the stimulated echo preparation period 21, the longitudinal nuclear magnetization is given by:

$$M_{z,FID} = \cos^2(\alpha) \cdot M_0$$

$$M_{z,STE} = \frac{1}{2} \sin^2(\alpha) \cdot M_0$$

$$M_{z,STE^*} = \frac{1}{2} \sin^2(\alpha) \cdot M_0,$$

where $M_{z,FID}$ denotes the unprepared (i.e. in-phase) longitudinal magnetization, and $M_{z,STE}$ and $M_{z,STE*}$ denote the two mirrored stimulated echo prepared (i.e. de-phased) longitudinal magnetization contributions. The transverse magnetization components (i.e. the FID from the first RF pulse α, the FID and the spin echo from second RF pulse α) are spoiled by a strong crusher gradient and will not be further considered. Hence, the reading RF pulse β of the imaging sequence generates three transverse signal contributions:

$$I_{FID}=S \cdot C(t)\sin(\beta)M_{z,FID}$$

$$I_{STE}=S \cdot C(t-T_S)\sin(\beta)M_{z,STE}$$

$$I_{STE*}=S \cdot C(t+T_S)\sin(\beta)M_{z,STE*},$$

wherein S represents a complex system constant, which comprises e.g. transmit and receive coil sensitivities for a given voxel, and β is the nominal flip angle of the reading RF pulse. Again, C describes the signal de-phasing for a given voxel due to the PRF shift:

$$C(t) = \int_V \rho(r) e^{-i\omega(r)t} dr,$$

wherein ρ and ω denote proton density and temperature-induced frequency offset, and the integral describes the summation over the given voxel.

For the purpose of temperature mapping according to the invention, the temperature-induced phase shift may be determined in this embodiment from the product of the conjugate stimulated echo signal $I_{STE*}$ and the complex conjugated stimulated echo signal $I^*_{STE}$:

$$\Phi = \arg(I_{STE*} \cdot I^*_{STE})$$

Therein, the effective PRF shift encoding time $t_{PRF,eff}$ is:

$$t_{PRF,eff}=2T_S-TE_{STE}+TE_{STE*}$$

The temperature map can be derived on this basis according to the PRF method by using the above formula for ΔT.

Spurious phase shifts from the transmit/receive chain of the used MR apparatus cancel out in these calculations. It is of advantage that the STE and the STE* signals stem from the same origin, have the same amplitude but differ in phase. The temperature information is derived from the phase difference of the STE and the STE* signals only. Hence, the FID signal is no longer required as reference signal as in the embodiment shown in FIG. 2. However, the FID signal, acquired at a short echo time, may still serve to reconstruct an anatomical image and/or as a reference for motion detection.

The problem of fat contamination of the PRF shift may be addressed in the above embodiments of the invention by applying fat saturation preparation pulses prior to the preparation period 21. Alternatively, the stimulated echo sequence itself may be made spectrally selective to encode the water signal only. This can be achieved by replacing one of the preparation RF pulses, preferably the second one, by a spectrally selective RF pulse to apply RF energy only to the water species. Both preparation RF pulses, and—not as efficiently—the RF pulses of the acquisition period 22 may be made chemical shift-selective to suppress the fat signal contribution.

While the STE signal $I_{STE}$ refocuses as a stimulated echo, the STE* signal $I_{STE*}$ further de-phases, and, hence, is therefore typically discarded in a conventional stimulated echo experiment. However, the imaging sequence shown in FIG. 3 employs tailored switched magnetic field gradients to acquire all three signal contributions as separate re-called gradient echoes at deliberately chosen echo times. The acquisition order (STE-FID-STE* or STE*-FID-STE) is determined by the polarity of the stimulated echo de-phaser gradient $G_{m2}$. Within the general sequence timing constraints resulting from e.g. acquisition bandwidth or RF and gradient power limitations, the gradient echoes times (i.e. time of the gradient echo top) may be independently selected to obtain a desired spectral encoding for the different echoes. For example, chemical shift effects can be encoded into the two different STE and STE* echo signals. Thus, a two point Dixon approach with flexible echo times (see Eggers et al., "Dual-echo Dixon imaging with flexible choice of echo times", MRM 2011, 65, 96-107, and Berglund et al., "Two-point dixon method with flexible echo times", MRM 2011, 65, 994-1004) may be applied on the MR images reconstructed from the STE* and STE signals to separate water and fat signals. Similar to conventional two-point Dixon, roughly in-phase/opposed-phase encoding times would be preferably chosen to optimize the stability of the approach. However, in contrast to conventional Dixon sequences, no change of the gradient polarity is required, which results in a shorter sequence and reduces odd/even eddy current related phase errors. After separation of water and fat contributions, the temperature map is derived only from the signal contributions from water spins to the acquired STE* and STE signals.

The invention claimed is:

1. A method of magnetic resonance (MR) imaging of an object placed in an examination volume of a MR device, the method comprising: subjecting the object to an imaging sequence of radio frequency (RF) pulses and switched magnetic field gradients, which imaging sequence is a stimulated echo sequence including: a) at least two preparation RF pulses radiated toward the object during a preparation period, and b) one or more reading RF pulses radiated toward the object during an acquisition period temporally subsequent to the preparation period; acquiring at least two MR signals during the acquisition period, wherein the two MR signals are either (i) a free induction decay (FID) signal and a conjugate stimulated echo signal or (ii) a stimulated echo signal and a conjugate stimulated echo signal; and deriving a temperature map using a proton resonance frequency shift that indicates a spatial distribution of the temperature within the object from the at least two acquired MR signals.

2. The method of claim 1, wherein the at least two preparation RF pulses each have a flip angle of 45°-90°.

3. The method of claim 1, wherein a plurality of FID signals and/or stimulated echo signals are generated by a corresponding plurality of consecutive reading RF pulses, each having a flip angle of less than 90°.

4. The method of claim 1, wherein the FID and stimulated echo signals are acquired as gradient-recalled echo signals.

5. The method of claim 1, wherein the temperature map is derived from a voxel-wise phase difference of the two acquired MR signals.

6. The method of claim 1, wherein the parameters of the imaging sequence are selected such that signal contributions from water spins and signal contributions from fat spins superimpose in the acquired MR signals in such a way as to allow reconstruction of separate water and fat images.

7. The method of claim 1, wherein a direct stimulated echo signal and a conjugate stimulated echo signal are acquired during the acquisition period, each at a different echo time.

8. The method of claim 1, wherein signal contributions from water spins and signal contributions from fat spins in the acquired MR signals are separated using a two- or multi-point Dixon technique.

9. The method of claim 8, wherein the temperature map is derived only from the signal contributions from water spins in the acquired MR signals.

10. The method of claim 1, wherein at least one RF pulse of the imaging sequence is spectrally selective to the MR resonance frequency of water spins.

11. The method of claim 1, wherein at least one fat saturation preparation RF pulse is radiated toward the object prior to the at least two preparation RF pulses of the stimulated echo sequence.

12. The method of claim 1, wherein a plurality of FID signals and/or stimulated echo signals are generated by a corresponding plurality of consecutive reading RF pulses, each having a flip angle of less than 45°.

13. The method of claim 1, wherein a plurality of FID signals and/or stimulated echo signals are generated by a corresponding plurality of consecutive reading RF pulses, each having a flip angle less than 30°.

14. A magnetic resonance (MR) device comprising at least one main magnet coil for generating a uniform, steady magnetic field within an examination volume, a number of gradient coils for generating switched magnetic field gradients in different spatial directions within the examination volume, at least one radio frequency (RF) coil for generating RF pulses within the examination volume and/or for receiving MR signals from an object positioned in the examination volume, a control unit for controlling the temporal succession of RF pulses and switched magnetic field gradients, and a reconstruction unit for reconstructing MR images from the received MR signals, wherein the MR device is arranged to perform the following steps: subjecting the object to an imaging sequence of RF pulses and switched magnetic field gradients, which imaging sequence is a stimulated echo sequence including: a) at least two preparation RF pulses radiated toward the object during a preparation period, and b) one or more reading RF pulses radiated toward the object during an acquisition period temporally subsequent to the preparation period; acquiring at least two MR signals during the acquisition period, wherein the two MR signals are either (i) a free induction decay (FID) signal and a conjugate stimulated echo signal or (ii) a stimulated echo signal and a conjugate stimulated echo signal; and deriving a temperature map using a proton resonance frequency shift that indicates a spatial distribution of the temperature within the object from the at least two acquired MR signals.

15. The device of claim 14, wherein the at least two preparation RF pulses each have a flip angle of 45°-90°.

16. The device of claim 14, wherein a plurality of FID signals and/or stimulated echo signals are generated by a corresponding plurality of consecutive reading RF pulses, each having a flip angle of less than 90°.

17. The device of claim 14, wherein the FID and stimulated echo signals are acquired as gradient-recalled echo signals.

18. The device of claim 14, wherein the temperature map is derived from a voxel-wise phase difference of the two acquired MR signals.

19. The device of claim 14, wherein a plurality of FID signals and/or stimulated echo signals are generated by a corresponding plurality of consecutive reading RF pulses, each having a flip angle of less than 45°.

20. A non-transitory computer medium comprising instructions stored therein for causing a computer processor to execute a computer on a magnetic resonance (MR) device, which computer program comprises instructions for: generating an imaging sequence of radio frequency (RF) pulses and switched magnetic field gradients, which imaging sequence is a stimulated echo sequence including: a) at least two preparation RF pulses radiated during a preparation period, and b) one or more reading RF pulses radiated during an acquisition period temporally subsequent to the preparation period; acquiring at least two MR signals during the acquisition period, wherein the two MR signals are either (i) a free induction delay (FID) signal and a conjugate stimulated echo signal or (ii) a stimulated echo signal and a conjugate stimulated echo signal; and deriving a temperature map using a proton resonance frequency shift that indicates a spatial distribution of temperature within an object from the at least two acquired MR signals.

* * * * *